United States Patent [19]
Ruddy et al.

[11] Patent Number: 5,476,646
[45] Date of Patent: * Dec. 19, 1995

[54] X-RAY CONTRAST COMPOSITIONS CONTAINING IODOPHENOXYALKANES AND PHARMACEUTICALLY ACCEPTABLE CLAYS

[75] Inventors: Stephen B. Ruddy, Schwenksville; Gregory L. McIntire, West Chester; Mary E. Roberts; John L. Toner, both of Downingtown, all of Pa.

[73] Assignee: Sterling Winthrop Inc., New York, N.Y.

[ * ] Notice: The portion of the term of this patent subsequent to Nov. 9, 2010, has been disclaimed.

[21] Appl. No.: 230,580

[22] Filed: Apr. 21, 1994

Related U.S. Application Data

[63] Continuation-in-part of Ser. No. 206,552, Mar. 4, 1994, Pat. No. 5,443,814, which is a continuation-in-part of Ser. No. 104,744, Aug. 11, 1993, Pat. No. 5,405,600, which is a continuation-in-part of Ser. No. 877,690, May 1, 1992, abandoned.

[51] Int. Cl.$^6$ .................................................. A61K 49/04
[52] U.S. Cl. .................... 424/9.45; 424/900; 514/473; 514/717; 514/941; 514/942; 568/580; 568/656
[58] Field of Search ........................... 424/5, 9.45, 900; 514/473, 717, 941, 942; 568/580, 656

[56] References Cited

U.S. PATENT DOCUMENTS

| | | | |
|---|---|---|---|
| 2,613,172 | 10/1952 | Galler | 167/95 |
| 2,622,100 | 12/1952 | Newbery et al. | 260/612 |
| 2,832,722 | 8/1958 | Singher | 167/95 |
| 3,795,698 | 3/1974 | Soulal et al. | 260/471 R |
| 4,038,379 | 7/1977 | Elinov et al. | 424/4 |
| 4,069,306 | 1/1978 | Rothman | 424/4 |
| 4,120,946 | 10/1978 | Quemille et al. | 424/4 |
| 4,588,574 | 5/1986 | Felder et al. | 423/554 |
| 4,692,325 | 9/1987 | Kritzler | 424/4 |
| 4,927,624 | 5/1990 | Bryant et al. | 424/9 |
| 5,019,370 | 5/1991 | Jay et al. | 424/4 |
| 5,107,842 | 4/1992 | Levene et al. | 128/662.02 |
| 5,260,049 | 11/1993 | Illig et al. | 424/5 |
| 5,277,896 | 1/1994 | Balkus, Jr. | 424/9 |
| 5,326,553 | 7/1994 | Illig et al. | 424/5 |
| 5,360,604 | 11/1994 | Ruddy et al. | 424/5 |

FOREIGN PATENT DOCUMENTS

| 1259565 | 9/1989 | Canada . |
|---|---|---|
| 1481943 | 5/1967 | France . |

OTHER PUBLICATIONS

Wang et al, Yaoxne Xuebao, vol. 16, No. 8, Aug.(1981), pp. 610–617.
James et al., Pharm. Acta Helvetiae, 47, 244–256, (1972).
Hashimoto et al, Japanese Kokai Patent Appl. No. Sho. 55-127322 (1980).

*Primary Examiner*—Gary E. Hollinden
*Attorney, Agent, or Firm*—Fish & Richardson

[57] ABSTRACT

Disclosed are x-ray contrast compositions for oral or retrograde examination of the gastrointestinal tract comprising a nonionic x-ray producing agent in combination with a pharmaceutically acceptable clay in a pharmaceutically acceptable carrier; and methods for their use in diagnostic radiology of the gastrointestinal tract.

20 Claims, No Drawings

X-RAY CONTRAST COMPOSITIONS CONTAINING IODOPHENOXYALKANES AND PHARMACEUTICALLY ACCEPTABLE CLAYS

This application is a continuation-in-part of application Ser. No. 08/206,552, filed on Mar. 4, 1994, U.S. Pat. No. 5,443,814 which in turn is a continuation-in-part of application Ser. No. 08/104,744, filed on Aug. 11, 1993, U.S. Pat. No. 5,405,600 which in turn is a continuation-in-part of application Ser. No. 07/877,690, filed on May 1, 1992.

BACKGROUND OF THE INVENTION

1. Field of the Invention

This invention relates to an x-ray contrast composition for oral or retrograde administration to a mammal comprising an x-ray contrast producing agent and a pharmaceutically acceptable clay.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

The most widely used contrast agents for the visualization of the GI tract is barium sulfate administered as a suspension orally or rectally as an enema. (See, for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor x-ray images. In the colon, when administered as an enema, it flocculates and forms irregular clumps with fecal matter.

Iodinated organic compounds have also been used as contrast agents since the iodine atom is an effective x-ray absorber. They have the most versatility and are utilized in the widest variety of procedures. They are very absorptive of x-rays with which the iodine interacts and produces a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos. 2,786,055; 3,795,698; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

These requirements were addressed by many investigators and their efforts resulted in great improvements over the years. The requirement of evenly coating the gut mucosa with, and sufficiently adhering thereto, a contrast agent to effectively cover the walls of the intestines proved to be rather difficult. Without meeting these requirements it is impossible to obtain x-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intraarterially.

While these polymeric materials greatly enhance attachment of the contrast agent used therewith to the walls of organs for better visualization thereof, there is still a need for an improved x-ray imaging medium that uniformly coats the soft tissues subjected to diagnostic x-ray examination.

We have now discovered that the use of certain natural clays in combination with an x-ray producing agent enhance the uniformity of coating on the gastrointestinal tract and the quality of x-ray images. In addition, these clays mask the unpleasant odor and taste of the x-ray contrast formulations as well as enhance the physical stability thereof.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an x-ray emitting device, a composition containing a pharmaceutically acceptable clay and an x-ray contrast agent. Such compositions must meet several requirements: both the x-ray contrast agent and the clay must be nontoxic; must not contain leachable or digestible components that would deleteriously affect the patient; and no components of the coating should be absorbed by, and pass through, the inner surface of the intestine.

The contrast agent and the pharmaceutically acceptable clay are incorporated in a liquid media for administration to a mammal for x-ray visualization of the GI tract.

The contrast agent utilized in the present invention is represented by the formula (I)

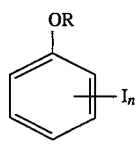
(I)

wherein R is a substituted or unsubstituted alkyl group containing from 2 to 8 carbon atoms, wherein said substituents are selected from the group consisting of $C_1$–$C_6$ alkyl, hydroxy and alkoxy; and n is 1 to 5.

Preferred contrast agents of the present invention have the formula:

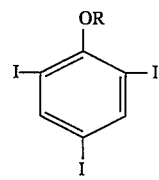

wherein R is a secondary alkyl group containing from 4 to 8 carbon atoms.

The most preferred contrast agent utilized by the present invention is the sec-octyl ether of 2,4,6-triiodophenol having the formula:

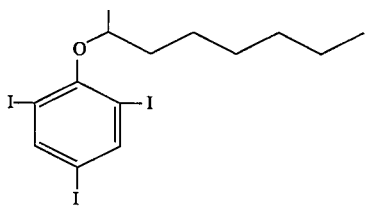

The compounds are readily synthesizable by methods known in the prior art. The compounds' desirable properties include: sufficient iodine content for producing adequate imaging; ability to coat the mucosal lining of the GI tract giving good imaging quality; and superior toxicological profile.

The compositions may be in the form of dispersions, suspensions when the x-ray contrast agent is a solid, or emulsions when the x-ray contrast agent is an oil; we prefer to use emulsions as the preferred embodiment.

The natural clays incorporated in the compositions of the present invention are selected from the group consisting of montmorillonite, beidelite, nontronite, hectorite and saponite.

DETAILED DESCRIPTION OF THE INVENTION

The contrast agents utilized in the compositions of the present invention are slightly soluble in water, having a partition coefficient equal or greater than 10. This degree of solubility allows the formation of stable formulations in the form of emulsions and suspensions when the formulations contain the requisite excipients. The term "stable" means that there is no separation of the ingredients contained in the compositions after oral or rectal administration thereof and during radiological examination of the GI tract. The slight solubility of the contrast agents in aqueous media permits diffusion of the contrast agents into the intestinal mucosa and secretions thereby forming a coating on the intestines. On the other hand, due to their slight solubility, the absorption of the contrast agent into the intestinal walls is minimal which reduces the possibility of toxic side effects.

Some of the contrast agents of the present invention can be prepared as described in U.S. Pat. No. 2,622,100, the disclosure of which is incorporated herein by reference. We, however, prefer utilizing the preparative methods described in the examples that follow.

EXAMPLE 1

A. 2-Mesyloxyoctane

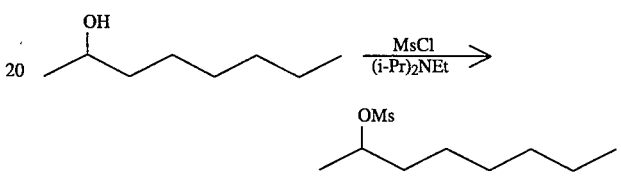

To 130 g (0.995 mol) of 2-octanol and 207 ml (1.19 mol, 1.2 equiv) of diisopropylethylamine in 1.5 L dichloromehane at 0° C. under a $CaSO_4$ drying tube was added dropwise 84.4 ml (1.09 mol, 1.1 equiv.) of methanesulfonyl chloride over 1 hour while keeping the internal temperature at less than 5° C. The faintly yellow solution was stirred at 0° C. for an additional 1.5 h. The cold reaction solution was then washed with 2×1 L ice-cold 1M HCl and 1 L of ice-cold $H_2O$ and brine and dried over $MgSO_4$. The residue was filtered through Celite and concentrated in vacuo below 35° C. to afford 208 g of a yellow oil. The yellow oil was placed under high-vacuum for 2 h at 25° C. to give 205 g of yellow oil. NMR spectra confirmed the desired title-product having only trace amounts of solvents present.

B. 2,4,6-Triiodophenox-2-Otane

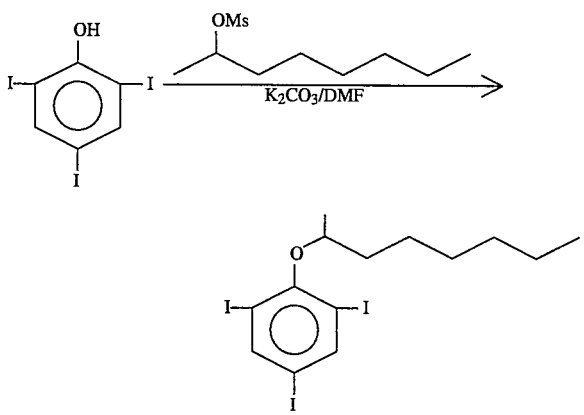

To a 5 L round bottom flask equipped with a mechanical stirrer was added, under nitrogen, 71.3 g (0.342 mol) of 2-mesyloxyoctane (obtained in A), 193 g (0.410 mol, 1.2 equiv) of 2,4,6-triiodophenol, 56.7 g (0.410 mol, 1.2 equiv.) of anhydrous potassium carbonate and 2.00 L of dimethylformamide (hereinafter DMF). The mixture was warmed slowly over one hour to reach a temperature of 55° C. to 60°

C. and then stirred at 55° C. for 16 hours.

The temperature was raised to 65° C. and the mixture stirred for an additional 4 hours, then slowly cooled to room temperature and filtered through Celite to remove solids. The amber-colored DMF filtrate was extracted with 3×500 ml hexane to remove some of the product (first extract). TLC (25% EtOAc-hexane) indicated that the extract was the extremely pure title-product.

The DMF solution remaining after extraction with hexane was diluted with 9 L $H_2O$ and 1 L of 1M NaOH. This mixture was extracted with 3×750 ml hexane (second extract). TLC showed that the extract was somewhat less pure than the first extract, but still only contained minor impurities.

The first extract and second extract were then separately washed with 2×500 ml of 1M NaOH, 500 ml of $H_2O$, 500 ml of saturated $Na_2SO_3$, 4×1 L $H_2O$, 1 L of brine and dried over $Na_2SO_4$.

Concentration in vacuo followed by high vacuum afforded from the first extract 65.5 g of a faintly yellow oil (33% yield). NMR spectra confirmed the extremely pure title-product containing no measurable amount of other materials, such as unreacted mesylate.

The second extract afforded 92.2 g (46% yield) of a light amber-colored oil. NMR spectra confirmed a reasonably pure product having only trace amounts of impurities, such as mesylate.

The 65.5 g of product obtained from the first extract was filtered through 500 g of silica eluting with 6 L of hexane to remove the trace of yellow color. Concentration in vacuo and under high vacuum and warming for 15 minutes afforded 64.7 g of the pure, colorless oil (99% recovery). NMR spectra confirmed the same very pure product as before.

The 92.2 g of product obtained from the second extract was subjected to the same procedure as the first extract. The product was found to be pure (98% recovery) without having a yellow color and without trace amounts of impurities, such as mesylate.

Example 2

2,4,6-Triiodophenoxy-2-Butane

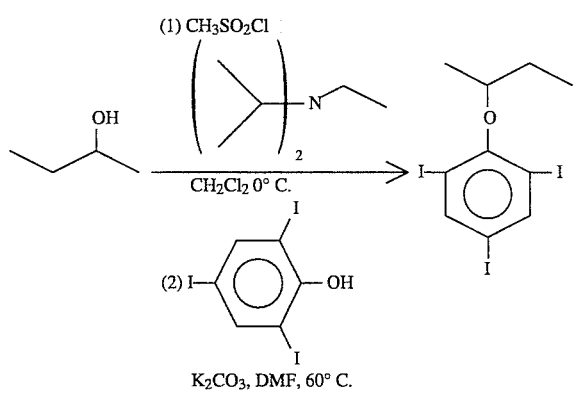

To a solution of 45.0 mmol of 2-butanol (4.1 ml) in dichloromethane at 0° C. was added 1.2 equiv. (9.4 ml) of diisopropylethylamine. After about 10 minutes, 1.1 equiv. (4.8 ml) of methanesulfonyl chloride was added slowly by syringe over about 10 min. The solution was stirred in an ice/water bath for 2.5 h, then poured over cold 5% HCl. The layers were separated and the organic layer was washed with cold 5% aqueous HCl and brine and dried over $Na_2SO_4$. The dried residue was dissolved in DMF (100 ml) and 50.0 mmol (23.6 g) of 2,4,6-triiodophenol was added which was followed by the addition of 50.0 mmol (6.9 g) of potassium carbonate. (The solution at this point turned dark and was difficult to stir). Stirring continued for 17 h. The solution was then cooled, filtered through Celite using DMF. The so-obtained DMF-containing solution was twice extracted with hexane, diluted with 200 ml of 0.1M aqueous NaOH and again extracted twice with hexane. The hexane extracts were combined and washed with 2×50 ml 1M NaOH, 2×50 ml $H_2O$ and brine. The organic layer was dried over $Na_2SO_4$, filtered and the solvent removed in vacuo. Purification of the residue by flash column chromatography (silica, hexanes) gave 9.9 g of the title product as an oil.

An alternate method of making the compound of Example 2 is described in Example 3.

Example 3

2,4,6-Triiodonhenoxy-2-Butane

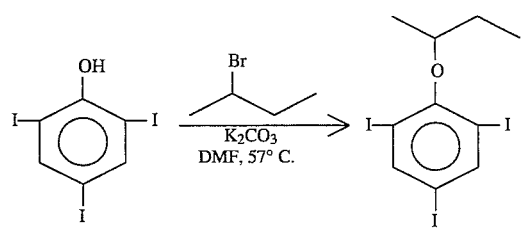

To a solution of 21.19 mmol( 10.0 g) of 2,4,6-triiodophenol in 40 ml (0.5M) DMF at room temperature was added 2.0 equiv (4.6 ml) of 2-bromobutane and 2.0 equiv. (5.86 g) of potassium carbonate. The mixture was heated to 57° C. in an oil bath and stirred for 65 h. The mixture was then cooled, filtered through Celite by washing with DMF. The DMF-containing solution was extracted with hexane, diluted with 10% NaOH (100 ml) in $H_2O$, and extracted 3 times with hexane. The extracts were combined and washed twice with 1M NaOH, twice with $H_2O$ and twice with brine. The organic layer was dried over $Na_2SO_4$, filtered and the solvent was removed in vacuo. Purification by flash column chromatography (hexanes, silica) yielded 10.83 g of the title product in the form of an oil.

Example 4

2,4,6-Triiodophenoxy-2-Hexane

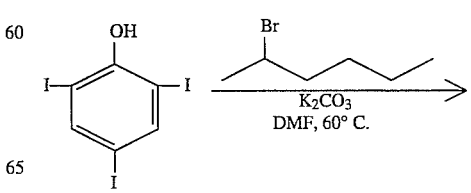

-continued

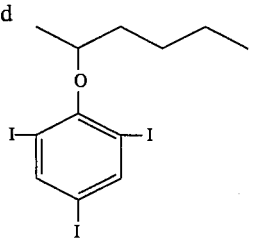

To a solution of 63.6 mmol (30 g) of 2,4,6-triiodophenol in 125 ml of DMF (0.5M) at room temperature was added 1.2 equiv. (10.8 ml) of 2-bromohexane and 1.5 equiv. (13.2 g) of potassium carbonate. The mixture was heated to 58° C. over 1.5 h, then stirred 40 h. The reaction mixture was filtered through Celite using DMF. The volume of DMF was reduced to 200 ml by evaporation in vacuo. The mixture was extracted twice with hexane, diluted with 500 ml of 10% NaOH in $H_2O$ and extracted again with hexane 3 times. The hexane extracts were then combined and washed twice with 1M NaOH, twice with $H_2O$ and once with brine. The organic layer was then dried over $Na_2SO_4$, filtered and the solvent was removed in vacuo. Flash column chromatography (hexanes, silica) yielded 31.5 g of the title compound in the form of an oil.

Example 5

4-Iodophenoxy-2-Octane

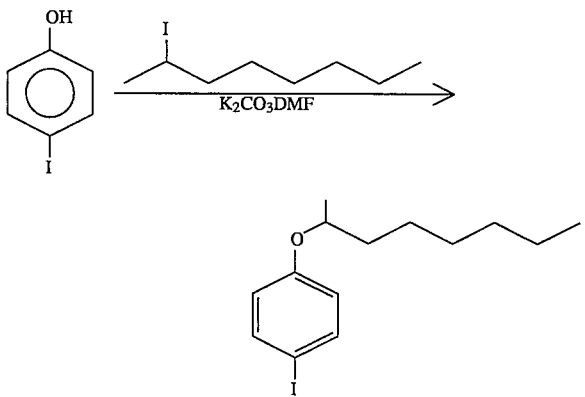

A mixture of 50.0 g (0.227 mol) of 4-iodophenol, 45.4 g (0.189 mol) of 2-iodooctane and 94.1 g (0.681 tool) potassium carbonate in 500 ml dry acetonitrile was heated to reflux under nitrogen and stirred for 20 h. The mixture was cooled and filtered through Celite and concentrated in vacuo. The brown residue was partitioned between 1 L hexanes and 500 ml 1M NaOH. The hexane layer was then washed with 1M NaOH (3×250 ml) saturated sodium sulfite (250 ml), water (250 ml) and brine (250 ml). The faintly yellow solution was dried over $Na_2SO_4$ and concentrated in vacuo to 34.3 g of a light yellow oil. The material in 60 ml of hexane was passed through a 600 g pad of silica gel eluting with 3% ethyl acetate-hexanes until just prior to elution of the yellow color. Concentration and warming under high vacuum afforded 26.9 g (43%) of product as a mobile colorless oil.

Other compounds of formula I may be prepared using the reaction techniques described in Examples 1 through 5 using appropriate starting materials and reagents. It is to be understood that all reaction conditions, including choice of solvents, reaction atmosphere, reaction temperature, duration of the experiment and workup procedures, are chosen to be conditions standard for that reaction, which should be readily recognized by one skilled in the art. It is understood by one skilled in the art of organic synthesis that the functionality present on portions of the educt molecule must be compatible with the reagents and reactions.

Starting materials, reagents and solvents used in the synthesis of the contrast agents can be obtained from chemical suppliers, such as Aldrich, Baker and Eastman Chemical Companies, or they may be prepared by techniques known in the prior art.

The natural, pharmaceutically acceptable clays incorporated in the present invention comprise aluminum silicates. They are used in purified form, suitable for administration to patients. The natural, pharmaceutically acceptable clays of the present invention, generally referred to as smectities, consist of dioctohedral smectites and trioctahedral smectites.

Dioctahedral smectites include:

montmorillonite, having the formula $$M^+Al_{3y}(FeMg)_ySi_4O_{10}(OH)_2.nH_2O;$$

beidelite, having the formula $$M^+(Al_2(Si_{4-x}Al_x)O_{10}(OH)_2.nH_2O;$$

nontronite, having the formula $$M^+(Fe_2^{3+}(Si_{4-x}Al_x)O_{10}(OH)_2.nH_2O;$$

wherein $M^+$ is Na, Ca or Mgo
Trioctahedral smectites include:
saponite, having the formula $$M^+(Mg_{3-y}(AlFe)_y)Si_{4-x}Al_x)O_{10}(OH)_2.nH_2O;\ \text{and}$$

hectorite, having the formula $$M^+(Mg_{3-y}Li_y)Si_4O_{10}(OH)_2.nH_2O;$$

wherein $M^+$ is Na, Ca or Mg.

The clays are available from chemical suppliers, such as, for example, American Colloid Company, Arlington Heights, Ill., under the tradenames:

MAGNABRITE®HS;

HECTABRITE®DP,

HECTABRITE®LT,

CARMARGO®White,

POLARGEL®NF,

POLARGEL®HV, and

VOLCLAY®NF-BC.

Other suppliers include: Engelhard Corp., Iselin, N.J.; Ashland Chemical Inc., Colombus, Ohio; RT Vanderbilt Co., Inc., Norwalk, Conn. and Whittaker Clark & Daniels, Inc., S. Plainfield, N.J.

The contrast agent and the pharmaceutically acceptable clay are formulated for administration using physiologically acceptable carriers or excipients in a manner within the skill of the art. The contrast agent with the addition of pharmaceutically acceptable aids (such as surfactants and emulsifiers) and excipients may be suspended or emulsified in an aqueous medium resulting in a suspension or emulsion.

Compositions

Compositions of the present invention comprise the following pharmaceutically acceptable components based on % w/v:

| Ingredients | Broad Range | Preferred Range | Most Preferred Range |
| --- | --- | --- | --- |
| Contrast agent | 5–45 | 10–35 | 15–25 |
| Clay | 0.1–10 | 0.5–5 | 1–2 |
| Surfactant | 1–20 | 2–10 | 3–5 |
| Excipients | 0–15 | 0.5–5 | 1–2 |
| Water - q.s. to 100% by volume | | | |

Excipients contemplated by the present invention include antifoaming agents, such as simethicone, siloxyalkylene polymers and polyoxyalkylated natural oils; preservatives, such as methyl paraben, propyl paraben, benzoic acid and sorbic acid; flavoring/sweetening agents, such as sodium saccharine; and coloring agents, such as lakes and dyes.

While the iodophenoxyalkanes of the present invention in formulations with a pharmaceutically acceptable vehicle provide good quality x-ray images, the addition of a pharmaceutically acceptable clay to the formulations greatly increases the quality of the x-ray images. At the low extreme of the concentration range there is little or no benefit gained, while above the higher extreme of the concentration range the formulation is too viscous for administration.

The following formulation examples will further illustrate the invention.

Example 6

| Components | |
| --- | --- |
| 2,4,6-triiodophenoxy-2-butane | 20.0 g |
| HECTABRITE ® DP | 1.45 g |
| Sorbitan monostearate | 0.5 g |
| Polysorbate 60 | 1.0 g |
| Poloxamer 338 | 5.0 g |
| Sodium Saccharine | 0.25 g |
| Benzoic acid | 0.50 g |
| Sorbic Acid | 0.050 g |
| Water q.s. to make 100 ml | |

Example 7

| Components | |
| --- | --- |
| 4-Iodophenoxy-2-octoane | 22.5 g |
| POLARGEL ® NF | 2.25 g |
| Sorbitan mono-oleate | 0.40 g |
| Polysorbate 20 | 1.25 g |
| Polyvinyl alcohol | 4.50 g |
| Sodium Saccharine | 0.25 g |
| Simethicone emulsion (food-grade) | 0.10 g |
| Water q.s. to make 100 ml | |

Example 8

| Components | |
| --- | --- |
| 2,4,6-triiodophenoxy-2-hexane | 18.5 g |
| MAGNABRITE ® HS | 1.25 g |
| Sorbitan monopalmitate | 0.6 g |
| Polyoxyethylene myristyl ether | 0.6 g |
| Polyvinylpyrrolidone | 3.5 g |
| Vanilla flavoring (artificial) | 0.25 g |
| Strawberry flavoring (artificial) | 0.25 g |
| Sorbitol | 1.0 g |
| Water q.s. to make 100 ml | |

The surface active agents used in the present invention may be cationic, anionic, nonionic or zwitterionic.

Suitable cationic surfactants include cetyl trimethyl ammonium bromide, cetyl pyridinium chloride, myristyl gamma picolinium chloride and benzalkonium chloride. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino adds having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritating than the cationic or anionic surfactants. Nonionic surfactants include carboxylic esters, carboxylic amides, ethoxylated alkylphenols, ethoxylated aliphatic alcohols, ethylene oxide polymer or ethylene oxide/propylene oxide co-polymers polyvinylpyrrolidone and polyvinylalcohol.

One particular type of carboxylic ester nonionic surface active agents are the partial, for example mono-, esters formed by the reaction of fatty and resin acids, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters are the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:

(a) Sorbitan esters (sold under the trade name Span) having the formula:

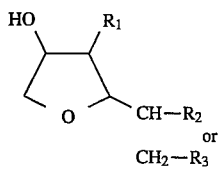

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})$ COO for laurate, $(C_{17}H_{33})$ COO for oleate, $(C_{15}H_{31})$ COO for palmitate, $(C_{17}H_{35})$ COO for stearate;

(b) Polyoxyethylene alkyl ethers (i.e. Brijs) having the formula:

where (x+1) is the number of carbon atoms in the alkyl chain, typically:

12 lauryl (dodecyl)
14 myristyl (tetradecyl)
16 cetyl (hexadecyl)
18 stearyl (octadecyl)

and y is the number of ethylene oxide groups in the hydrophilic chain, typically 10–60;

(c) Polyoxyethylene sorbitan fatty acid esters, sold under the trade names of Tween or Polysorbates 20, 40, 60, 65, 80 & 85 having the formulas (1) and (2)

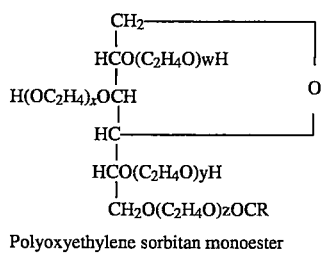

Polyoxyethylene sorbitan monoester

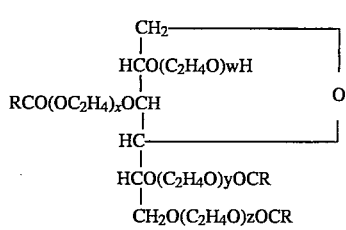

Polyoxyethylene sorbitan triester wherein w+x+y+z=20 (Polysorbate 20, 40, 60, 65, 80 and 85)
w+x+y+z=5 (Polysorbate 81)
w+x+y+z=4 (Polysorbate 21 and 61).

(d) Polyoxyethylene stearates, such as:
poly(oxy-1,2-ethanediyl),α-hydro-ω-hydroxy-octadecanoate;
polyethylene glycol monostearate; and
poly(oxy-1,2-ethanediyl)-α-(1-oxooctadecyl)-ω-hydroxy-polyethylene glycol monostearate.

(e) Polyethylene oxide/polypropylene oxide block copolymers, sold under the name PLURONIC™, which include Poloxamer 407 (PLURONIC® F127), Poloxamer 188 (PLURONIC® F68), Poloxamer 237 (PLURONIC® F87) and Poloxamer 338 (PLURONIC® F108).

(f) Polyvinylpyrrolidone.

(g) Polyvinylalcohol.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

When administered to mammals, the compositions of the present invention produce excellent x-ray and CT images.

The invention, having been fully described, it will be apparent to one skilled in the art that changes and modifications can be made thereto without departing from the spirit and scope thereof.

What is claimed is:

1. An x-ray contrast composition for oral or retrograde examination of the gastrointestinal tract comprising on a % weight per volume basis:

(a) from about 5 to 45% of an x-ray contrast producing agent having the formula, or a pharmaceutically acceptable salt thereof $$\text{(I)}$$

[structure: phenyl ring with OR substituent and $I_n$]

wherein

R is a substituted or unsubstituted alkyl group containing from 2 to 8 carbon atoms, wherein said substituents are selected from the group consisting of $C_1-C_6$ alkyl, hydroxy and alkoxy; and n is 1 to 5;

(b) from about 0.1 to 10% of a pharmaceutically acceptable clay selected from the group consisting of: montmorillonite, beidelite, nontronite, hectorite and saponite;

(c) from about 1.0 to 20% of a surfactant selected from the group consisting of nonionic, anionic, cationic and zwitterionic surfactants;

(d) from about 0 to 15% of an excipient; and (e) water to make 100% by volume.

2. The x-ray contrast composition of claim 1 wherein said x-ray contrast producing agent is present in an amount of from about 10 to 35%.

3. The x-ray contrast composition of claim 1 wherein said pharmaceutically acceptable clay constitutes from 0.5 to 5% of the composition.

4. The x-ray contrast composition of claim 1 wherein said surfactant constitutes from 2 to 10% of the composition.

5. The x-ray contrast composition of claim 1 wherein said excipient constitutes from 0.5 to 5% of the composition.

6. The x-ray contrast composition of claim 1 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide copolymer, polyvinylpyrrolidone and polyvinylalcohol.

7. The x-ray contrast composition of claim 1 wherein said surfactant is sorbitan ester having the formula:

[structure: tetrahydrofuran ring with HO, $R_1$, $CH-R_2$ or $CH_2-R_3$ substituents]

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})$ COO for laurate, $(C_{17}H_{33})$ COO for oleate, $(C_{15}H_{31})$ COO for palmitate or $(C_{17}H_{35})$ COO for stearate.

8. The x-ray contrast composition of claim 1 wherein said surface active agent is polyoxyethylene stearate.

9. The x-ray contrast composition of claim 1 wherein said surfactant is polyoxyethylene sorbitan fatty acid ester of formulas (1) and (2)

$$\text{(1)}$$

[structure]
CH$_2$—
HCO(C$_2$H$_4$O)$_w$H
H(OC$_2$H$_4$)$_x$OCH       O
HC—
HCO(C$_2$H$_4$O)$_y$H
CH$_2$O(C$_2$H$_4$O)$_z$OCR Polyoxyethylene sorbitan monoester $$\text{(2)}$$

CH$_2$—
HCO(C$_2$H$_4$O)$_w$H
RCO(OC$_2$H$_4$)$_x$OCH      O
HC—
HCO(C$_2$H$_4$O)$_y$OCR
CH$_2$O(C$_2$H$_4$O)$_z$OCR

Polyoxyethylene sorbitan triester wherein the sum of w+x+y+z is selected from the group consisting of 4, 5 and 20.

10. The x-ray contrast composition of claim 1 wherein said x-ray contrast producing agent is selected from the group consisting of: 2,4,6-triiodophenoxy-2-octane, 2,4,6-triiodophenoxy-2-butane, 2,4,6-triiodophenoxy-2-hexane and 4-iodophenoxy-2-octane.

11. A method of carrying out x-ray examination of the gastrointestinal tract of a patient, said method comprises the oral or rectal administration to the patient an x-ray contrast formulation comprising:

(a) from about 5 to 45% of an x-ray contrast producing agent having the formula, or a pharmaceutically acceptable salt thereof $$\text{(I)}$$

[structure: phenyl ring with OR substituent and $I_n$]

wherein

R is a substituted or unsubstituted alkyl group containing from 2 to 8 carbon atoms, wherein said substituents are selected from the group consisting of $C_1-C_6$ alkyl, hydroxy and alkoxy; and n is 1 to 5;

(b) from about 0.1 to 10% of a pharmaceutically acceptable clay selected from the group consisting of montmorillonite, beidelite, nontronite, hectorite and saponite;

(c) from about 1.0 to 20% of a surfactant selected from the group consisting of nonionic, anionic, cationic and zwitterionic surfactants;

(d) from about 0.0 to 15% of an excipient; and (e) water to make 100% by volume.

12. The method of claim 11 wherein said x-ray contrast producing agent is present in an amount of from about 10 to 35%.

13. The method of claim 11 wherein said pharmaceutically acceptable clay constitutes from 0.5 to 5% of the composition.

14. The method of claim 11 wherein said surfactant constitutes from 2 to 10% of the composition.

15. The method of claim 11 wherein said excipient constitutes from 0.5 to 5% of the composition.

16. The method of claim 11 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide co-polymer, polyvinylpyrrolidone and polyvinylalcohol.

17. The method of claim 11 wherein said surfactant is sorbitan ester having the formula:

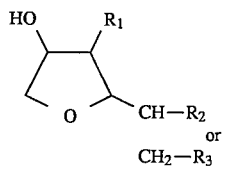

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})$ COO for laurate, $(C_{17}H_{33})$ COO for oleate, $(C_{15}H_{31})$ COO for palmitate or $(C_{17}H_{35})$ COO for stearate.

18. The method of claim 11 wherein said surface active agent is polyoxyethylene stearate.

19. The method of claim 11 wherein said surfactant is polyethylene sorbitan fatty acid ester of formulas (1) and (2)

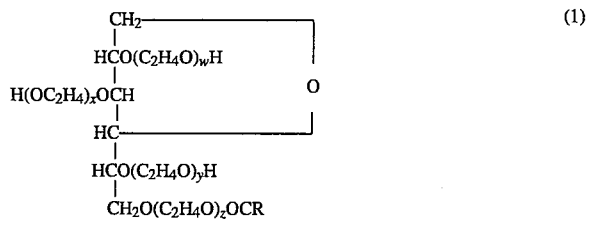

Polyoxyethylene sorbitan monoester

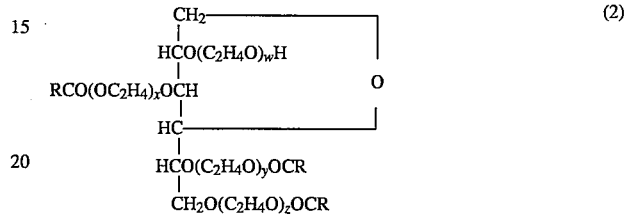

Polyoxyethylene sorbitan triester wherein the sum of w+x+y+z is selected from the group consisting of 4, 5 and 20.

20. The method of claim 11 wherein said x-ray producing agent is selected from the group consisting of: 2,4,6-triiodophenoxy-2-octane, 2,4,6-triiodophenoxy-2-butane, 2,4,6-triiodophenoxy-2-hexane and 4-iodophenoxy-2-octane.

* * * * *